United States Patent [19]

English

[11] Patent Number: 5,071,654

[45] Date of Patent: Dec. 10, 1991

[54] ION CHANNEL PROPERTIES OF DELTA ENDOTOXINS

[75] Inventor: Leigh H. English, Newtown, Pa.

[73] Assignee: Ecogen Inc., Langhorne, Pa.

[21] Appl. No.: 436,145

[22] Filed: Nov. 13, 1989

Related U.S. Application Data

[63] Continuation-in-part of Ser. No. 193,602, Sep. 1, 1988, abandoned.

[51] Int. Cl.$^5$ .................... A01N 63/02; A61K 37/02; C12Q 1/02; C07K 15/02
[52] U.S. Cl. .................................. 424/405; 424/93; 424/450; 435/29; 435/252.31; 530/324; 530/825
[58] Field of Search ............. 424/450, 93, 405; 530/324, 825; 71/9; 435/29, 252.31

[56] References Cited

U.S. PATENT DOCUMENTS

| | | | |
|---|---|---|---|
| 4,532,089 | 7/1985 | MacDonald | 424/450 |
| 4,652,628 | 3/1987 | Walfield et al. | 530/324 |
| 4,774,085 | 9/1988 | Fidlar | 424/85.5 |

OTHER PUBLICATIONS

Ellar, Abstract from Soc. Invert. Path. XII Annual Meeting, College Park, Md., Aug. 1989.
Haider et al., *Biochim. Biophys. Acta* (1989) 978:216-222.
Ellar, Amer. Chem. Soc. 198th Natl. Meeting, Abstract No. 114, Division of Agrochemicals, Miami Beach, Fla., Sep. 10-15 1989.
Höfte et al., *Microbiolog. Rev.* (Jun 1989) 53:242-255.
English et al., *Insect Biochem.* (1989) 19:145-152.
Hofmann et al., *Proc. Natl. Acad. Sci. U.S.A.* (Nov. 1988) 85:7844-7848.
Wolfersberger, Soc. Invert. Path. Meeting Abstract, No. 118, San Diego, Calif., Aug. 1988.
Crawford et al., *J. Exp. Biol.* (1988) 137:277-286.
Hofmann et al., *Eur. J. Biochem.* (1988) 173:85-91.
Crawford et al., Soc. Invert. Path. XX Annual Meeting Abstract Gainesville, Fla., Jul. 1987.
Knowles et al., *Biochim. Biophys. Acts* (1987) 924:509-518.
Haider et al., *Biochem. J.* (1987) 248:197-201.
Wolfersberger et al., *Comp. Biochem. Physiol.* (1987) 86A:301-308.
English et al., *J. Biol. Chem.* (1986) 261:1170-1173.
Wolfersberger et al., *Zentralbl. Bakteriol. Mikrobiol. Hyg. Supp.* (1986) 15:237-238.
Lüthy et al., *Zentralbl. Bakteriol. Mikrobiol. Hyg. Supp.* (1986) 15:161-166.
Sacchi et al., *FEBS Lett.* (1986) 204:213-218.
Ellar et al., in Fundamental and Applied Aspects of Invertebrate Pathology (Samson et al., eds), 1986, pp. 7-10, Foundation of the 4th Intl. Colloquium of Invertebrate Pathology, Wageningen, The Netherlands.
Tse et al., *J. Biol. Chem.* (1985) 260:3506-3511.
Ellar et al., Molecular Biology of Microbial Differentiation, Hoch, ed., Am. Soc. Microb., 1985, pp. 230-240.
English et al., *J. Memb. Biol.* (1985) 85:199-204.
English et al., *J. Cell. Phys.* (1984) 121:125-132.
Charles et al., *Ann. Microbiol.* (Institut Pasteur) (1983) 134A:197-218.
Percy et al., *J. Invert. Pathol.* (1983) 41:86-98.
Jackson et al., *Biochem.* (1982) 21:5601-5608.
Lüthy et al., Pathogenesis of Invertebrate Microbial Diseases, Davidson, ed., Allanheld, Osmun, Totawa, N.J. (1981) pp. 235-267.
Bulla et al., *J. Biol. Chem.* (1981) 256:3000-3004.
Griego et al., *J. Invert. Pathol.* (1980) 35:186-189.
Harvey et al., *J. Exp. Biol.* (1979) 83:293-304.
Milne et al., *J. Invert. Path.* (1977) 29:230-231.
Kasahara et al., *J. Biol. Chem.* (1977) 252:7384-7390.
Brunner et al., *Biochim. Biophys. Acta* (1976) 455:322-331.
Racker, Proc. 10th FEBS Meet. (1975) pp. 25-34.
Racker, *Biochem. Biophys. Res. Com.* (1973) 55:224-230.

*Primary Examiner*—Thurman Page
*Assistant Examiner*—Carlos Azpuru
*Attorney, Agent, or Firm*—Christopher Egolf

[57] ABSTRACT

The present invention relates to an in vitro method for measuring the toxicity of a delta-endotoxin of *Bacillus thuringiensis* by evaluating the ability of said endotoxin to form an ion channel in a phospholipid vesicle.

16 Claims, 5 Drawing Sheets

Figure 1

ION CHANNEL PROPERTIES OF DELTA ENDOTOXINS

1.0 CROSS-REFERENCE TO RELATED APPLICATION

This is a continuation-in-part of U.S. patent application Ser. No. 193,602 filed Sept. 1, 1988, now abandoned.

1.1. FIELD OF THE INVENTION

This invention relates to the screening of the potency of delta endotoxin insecticides. More specifically, this invention presents an in vitro assay which can be used to assess the activity of such delta endotoxin insecticides by evaluating their ability to form trans-membrane channels. Such an assay permits rapid and unambiguous evaluation of insecticide potency, overcoming the error and time consuming difficulties of in vivo toxicity assays based on insect population analysis

2. BACKGROUND OF THE INVENTION

2.1. *Bacillus thuringiensis* and Crystal Toxins

Among the most widely used and commercially successful biopesticides are those which employ the microorganism *Bacillus thuringiensis*.

*Bacillus thuringiensis* is a widely distributed, rod shaped, aerobic and spore forming microorganism. During its sporulation cycle *B. thuringiensis* synthesizes proteins that aggregate to form parasporal crystals. The pathogenicity of *B. thuringiensis* to a variety of sensitive insects, such as larvae Lepidoptera (caterpillars), larvae Coleoptera (grubs) and larvae Diptera (mosquito larvae), is essentially due to these parasporal crystals, which may represent over 20% of the dry weight of the *B. thuringiensis* cell at the time of sporulation.

It has been reported that different varieties of *B. thuringiensis* produce serologically different parasporal crystals. Many varieties of B. thuringiensis produce a bipyramidal crystal composed of one or more closely related approximately 130-kDa proteins (P1 proteins or delta endotoxins) that are lepidopteran toxic. Several varieties also produce a flat, cuboidal crystal composed of a 66-kDa protein (P2 protein) that is both lepidopteran and dipteran toxic. *B. thuringiensis* var. israelensis produces an irregularly shaped parasporal crystal that is composed of three major proteins of approximately 130, 67 and 28 kDa. As in all cases, the size of *B. thuringiensis* protein toxins are only estimations based on the rates of migration of the proteins during electrophoresis through polyacrylamide gels. The var. israelensis crystal is toxic to dipteran larvae although there are conflicting data as to the toxic activity of the individual proteins that comprise the crystal. Other *B. thuringiensis* varieties have been discovered which produce a rhomboidal protein crystal that is toxic to coleopteran (beetle) insects.

In this disclosure, the terms "protein endotoxin", "delta endotoxin", "endotoxin" and "toxin" are used synonomously to refer to the crystal protein endotoxins produced by *Bacillus thuringiensis* insecticidal protein toxin genes, and are not intended to be limited to endotoxins produced by any specific Bt strain.

2.2.1 Action of Delta Endotoxins

The crystalline endotoxins of *B. thuringiensis* have been shown to have their primary effect on the epithelium of the insect gut. Within a few minutes after an insect's ingestion of crystals, feeding ceases, and movements are greatly reduced. The selectivity of the epithelial cell membrane to ions is also greatly reduced (Luthy et al., *Pathogenesis of Invertebrate Microbial Diseases,* Davidson, ed., pp.235-267, Allanheld Osmun, Totawa, N.J. 1981).

Histophathological observations of the effects of the endotoxins on a number of different insects show a very uniform pattern: the midgut cells swell, the microvilli become absorbed into the cells, the interior of the cells becomes highly vacuolated, and organelles, such as endoplasmic reticulum and mitochondria, gradually disintegate. This loss of vital function of the epithelium eventually leads to a free exchange of fluids between the hemocoel and the lumen of the gut (Luthy et al., supra,; Griego et al., *J.Invert.Pathol.* 35:186-189, 1980; Percy et al., *J.Invert.Pathol.* 41:86-98, 1983; Charles et al., *Ann. .Microbiol. Institute Pasteur* 134A:197-218, 1983).

The actual mechanism by which these endotoxins bring about such an effect has not heretofore been determined, although certain biochemical patterns have been observed in association with the toxins. A number of authors (Sacchi et al., FEBS Lett. 204:213-218, 1986; Wolfersberger et al., *Zentralbl.Bakteriol.Mikrobiol.Hyg.- Supp.* 15:237-238, 1986; Luthy et al., *Zentralbl.Bakteriol.Mikrobiol.Hyg.Supp.* 15:161-166, 1986; Harvey et al. *J. Exp.Biol.* 83:294-304, 1979) have made the observation that delta-endotoxins appear to enhance an electrical current carried by $K^+$ across the midgut epithelium between the lumen-side and the blood-side of the insect midgut By measuring the effects of delta-endotoxin on this current, it has been shown the the toxins have the ability to reverse the normal direction of $K^+$ transport across the midgut epithelium. Subsequent work has shown that this $K^+$ dependent current is inhibited by $Ba^+$, a known blocker of $K^+$ ionic channels (Crawford et al., *Abst. Soc. Invert Path.,* 1987).

Studies in mammalian systems have shown that an ion channel in an epithelial cell serves as an aid in maintaining the proper intracellular and extracellular composition by controlling the transport of ions through the cell membrane. Specifically, because of the hydrophobic nature of the lipid bilayer of the cell membrane, passive transport of ions can be achieved when the ion is ensconced in a polar cavity of a membrane-bound structure with a more lipophilic exterior. An integral membrane protein may provide a hydrophilic pathway for the passive ion transport if the internal polar cavity extends in a tunnel-like fashion through the membrane; such a transport route constitutes an ion channel. Examples of ion channels in mammalian systems include channels which function primarily as a $Na^+$ channel, a $Ca^{2+}$ channel, a $K^+$ channel or a $Cl^-$ channel. These channels are all integral membrane proteins capable of permitting the movement of at least one ion species across the cell or organelle membrane, but are not totally specific for one ion species.

The literature cited above concerning Bt toxin mode of action shows a strong circumstantial connection between the physiological activity of delta-endotoxin and a putative $K^+$ channel in the insect midgut epithelium. However, the exact relationship between the delta-endotoxin and the $K^+$ channel has not previously been determined. It has generally been assumed that the delta-endotoxin exerts its fatal effect by interfering with a preexisting ion channel present in the cells of the midgut epithelium. It has now been discovered that the delta-endotoxin itself forms the ion channel; this unexpected observation now provides the basis for the development of the present novel screening technique, described and claimed hereinafter, for evaluating the toxicity of delta endotoxins.

2.2 Insecticidal Toxicity Screening

A simple, rapid and unambiguous in vitro assay is needed to obtain proper quantitative data regarding delta-endotoxin activity. The present screening tests rely in large part in the use of living insects or on living insect cell lines. In addition to being time-consuming, the previously known tests, and in fact any type of test which relies on the observation of an in vivo result, is inherently susceptible to misinterpretation by virtue of the enormous number of variables which may control the result. For example, the quantity of a toxin that an insect consumes cannot be easily controlled. Mortality can be due to causes other than the toxin such as microbial pathogens which can contribute to mortality.

A preferred test would be one that is essentially purely mechanical, and which does not rely on living material. Until the present discovery of the direct mode of action of delta-endotoxin, such a test has not been possible. The knowledge that the toxin forms an ion channel has permitted construction of a screening test for Bt endotoxin insecticidal activity which completely eliminates the need for using living material to evaluate delta-endotoxin activity.

It is an object of this invention to provide a simple and accurate procedure for the qualitative and quantitative assay of the insecticidal potency of various delta endotoxins. The present procedure permits the evaluation of delta-endotoxin insecticidal activity without the necessity of employing living insects or cell lines as the basis of the test. The invention permits the rapid analysis of the insecticidal toxicity of delta-endotoxins by exploiting the ability of such delta-endotoxins to form ion channels.

3.0. SUMMARY OF THE INVENTION

In accordance with the present invention, the relative toxicities of *Bacillus thuringiensis*-type protein endotoxins in susceptible insects may be evaluated by the in vitro method of (i) combining a phospholipid and a Bt-type protein endotoxin, in activated form, under conditions in an aqueous medium that produce a phospholipid bilayer containing endotoxin incorporated therein; (ii) contacting one side of the endotoxin-containing phospholipid bilayer with an aqueous solution containing a monovalent cation to create an ion concentration gradient across the bilayer, at a temperature from about 15° C. to 35° C.; (iii) measuring the monovalent cation flow across the endotoxin-containing phospholipid bilayer; and (iv) comparing the cation flow for the endotoxin-containing bilayer with that of a control, selected from an endotoxin-free phospholipid bilayer or an otherwise identical phospholipid bilayer containing a second Bt-type protein endotoxin in lieu of the first endotoxin; whereby the propensity of the first protein endotoxin for forming an ion channel open to monovalent cation flow is determined.

In a preferred embodiment of this invention, the relative toxicities of *Bacillus thuringiensis*-type protein endotoxins in target insects may be evaluated by the in vitro method of (i) combining insect midgut brush border from a specific target insect and a phospholipid, under conditions in an aqueous medium that produce a hybrid phospholipid bilayer which incorporates the brush border therein; (ii) introducing a Bt-type protein endotoxin, in activated form, into contact with the hybrid phospholipid bilayer, so as to bind the endotoxin into the hybrid phospholipid bilayer; (iii) contacting one side of the endotoxin-treated hybrid phospholipid bilayer with an aqueous solution containing a monovalent cation to create an ion concentration gradient across the bilayer, at a temperature from about 15° C. to 35° C.; (iv) measuring the monovalent cation flow across the endotoxin-treated hybrid phospholipid bilayer; and (v) comparing the cation flow for the endotoxin-treated hybrid phospholipid bilayer with that of a control, selected from an endotoxin-free hybrid phospholipid bilayer or an otherwise identical hybrid phospholipid bilayer treated with a second Bt-type protein endotoxin in lieu of the first endotoxin; whereby the susceptibility of the target insect to the first protein endotoxin and the propensity of such endotoxin for forming an ion channel open to monovalent cation flow are determined.

In both of these methods, the phospholipid bilayer is preferably in the form of a phospholipid vesicle. In such cases, the monovalent cation flow may be determined by spectrophotometric light scattering, scintillation counting of radiolabelled cations, fluorescence intensity, atomic absorption, nuclear magnetic resonance or x-ray analysis. The monovalent cation flow may be measured directly or indirectly; in the latter case, osmotically induced water flow through the ion channel may be measured, via vesicle shrinkage or swelling, to evaluate ion channel formation.

In this invention, the formation of ion channels can be observed in vitro in synthetic phospholipid vesicles which mimic the membrane of the insect midgut epithelium. The quality of a channel formed by any given delta-endotoxin can thus be determined without using live insects. Instead, the ability to form a channel may be evaluated in a straightforward manner by physical measurements, preferably via monitoring monovalent cation flow, all within the synthetic phospholipid vesicle system.

The invention also includes the novel insecticidal composition of a phospholipid vesicle with *Bacillus thuringiensis* protein endotoxin incorporated therein and an agriculturally-acceptable carrier.

Another embodiment of this invention is the insecticidal composition of a phospholipid vesicle with insect midgut brush border and a *Bacillus thuringiensis* protein endotoxin incorporated therein and an agriculturally-acceptable carrier.

Such phospholipid vesicle compositions provide the vehicle for the application of delta endotoxin on plants. The vesicles may act in much the same fashion as liposomes do in vertebrates, to facilitate the delivery of the toxins to the target midgut cells in susceptible insects.

4.0. BRIEF DESCRIPTION OF THE FIGURES

FIG. 1 illustrates the pattern of uptake of the radiolabelled cation $^{86}Rb^{30}$, at 22° C. and a pH of 7.5, into phospholipid (soybean) vesicles containing Bt kurstaki activated endotoxin incorporated therein, compared with endotoxin-free vesicles.

5.0. DETAILED DESCRIPTION OF THE INVENTION

5.1. Basis of the Assay

Figure 2:
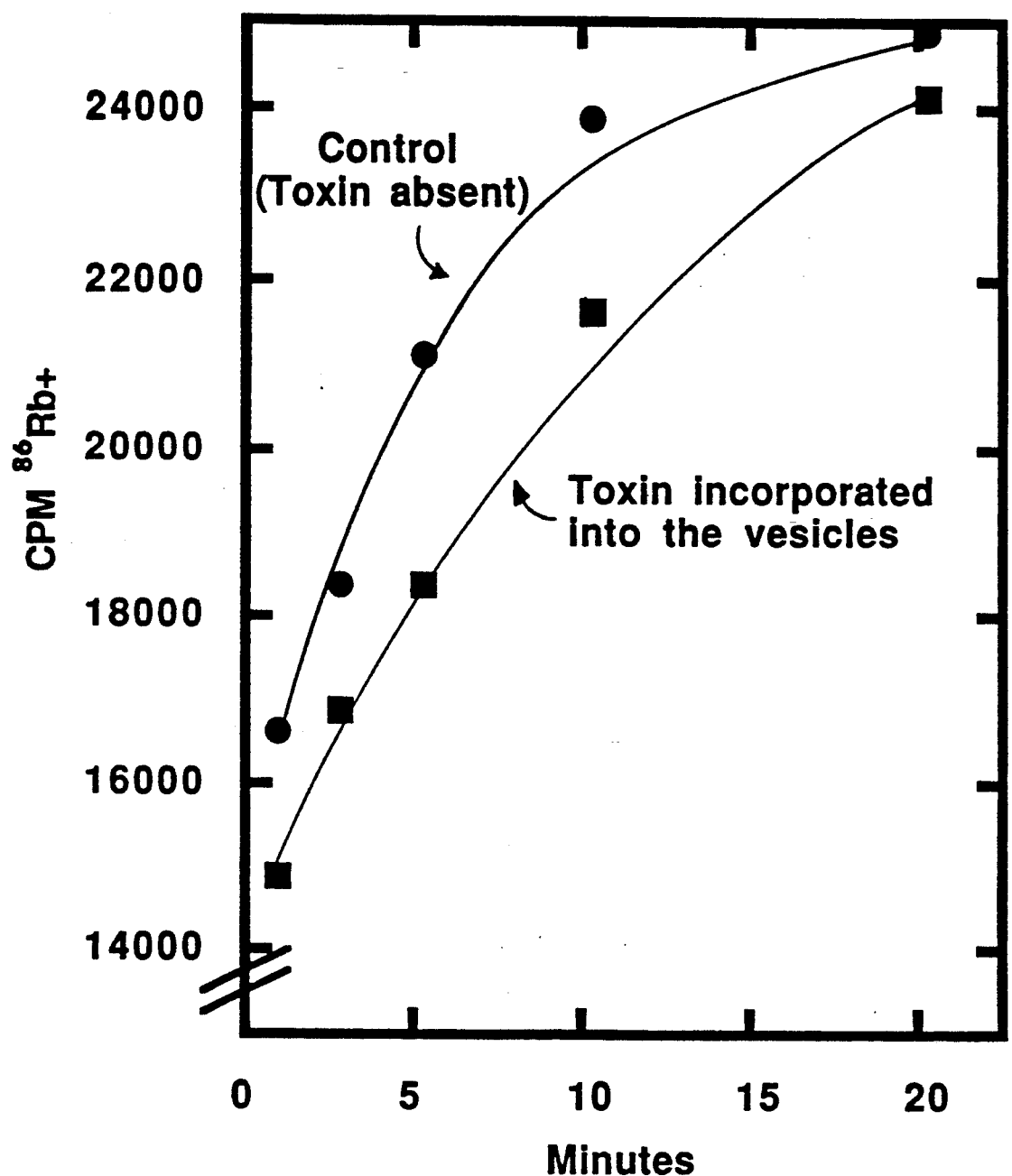
FIG. 2 illustrates the pattern of uptake of $^{86}Rb^{30}$, at 0° C. and a pH of 7.5, into phospholipid (soybean) vesicles containing Bt kurstaki activated endotoxin incorporated therein, compared with endotoxin-free vesicles.

The discovery that the delta-endotoxin itself is capable of forming an ion channel has now provided the ability to construct what is essentially a purely mechanical test system to assay toxin activity. With the recognition that the action of delta-endotoxin does not depend on its effect on a preexisting ion channel in the insect's midgut epithelium, the necessity of employing a living system is eliminated. Instead, an artificial membrane system, comprising phospholipid vesicles, and optionally additional proteins, particularly insect membrane proteins, can be employed to mimic the insect epithelial membrane, and to quantitate the ability of a given delta-endotoxin to form an ion channel therein. The channel forming ability is measured in one or more ways, e.g., preferably by measurement of rate and amount of monovalent cation influx into the vesicles.

Recognition of the mechanism of action of the *B. thuringiensis* delta-endotoxin and the present test system which incorporates endotoxin into phospholipid vesicles, has also provided an alternative means of utilizing the delta-endotoxin in an insecticidal composition. Although the encapsulation of drugs into liposomes is a well-established method of drug delivery in vertebrates, the encapsulation of insecticidal toxins, specifically *B. thuringiensis* delta-endotoxins in a phospholipid vesicle, has not previously been suggested as the basis for an insecticidal composition. The present understanding of the mechanism of action of the endotoxins, and the demonstrated interaction of the toxin with phospholipids in vivo suggests that the administration of delta-endotoxin in a phospholipid vesicle, as described herein for the assay system, may enhance the efficacy of the delta-endotoxin. Thus, the present invention also contemplates use of the novel phopholipid-toxin vesicles in an insecticidal composition, as a means of beneficiating the action of the toxin in vivo.

5.2. Formation of Phospholipid Vesicles

In preparing the phospholipid bilayer vesicles or planar phospholipid bilayers used in the present invention, virtually any phospholipid can be employed. These compounds are universally present in nature as a component of cell membranes, and a number of phospholipids are readily available commercially. Among these are phosphatidyl choline, phosphatidyl serine, phosphatidyl ethanolamine, phosphatidyl inositol and phosphatidyl glycerol. Phosphatidyl choline is very useful because of the simplicity of the system and is therefore preferred. Mixtures of phospholipids, many of which are commercially available such as soybean phospholipids, can also be employed. As will be described in more detail below, other components may be present along with the phospholipid. In a preferred embodiment of this invention, insect midgut brush border from the epithelial cells of a specific target insect may also be incorporated into the phospholipid bilayer.

It should be noted that in order for the assay to be performed correctly, the endotoxin must be physically incorporated into the vesicle or planar bilayer; if the endotoxin is simply added to the exterior of the phospholipid vesicle and is not thereafter incorporated into the phospholipid bilayer structure, the assay will not provide useful information. It should be noted, however, that contacting a phospholipid vesicle (or planar bilayer) with large amounts of endotoxin in excess of normal physiological concentrations, will result in the endotoxin becoming spontaneously incorporated into the vesicle and forming an ion channel. At lower endotoxin concentrations, the vesicles (or planar bilayer) must be physically manipulated to induce incorporation of the toxin into the phospholipid bilayer membrane, e.g., via a freeze-thaw-sonication procedure.

When insect midgut brush border is incorporated into the phospholipid bilayer, receptors in the brush border facilitate incorporation of endotoxin in contact with the bilayer exterior into the bilayer (provided that the brush border is obtained from a target insect susceptible to the *B. thuringiensis* endotoxin being evaluated). this functionality of the brush border makes it especially useful in the preferred method of this invention for evaluating the relative toxicities of Bt-type protein endotoxins in the target insect from which the brush border was obtained.

The source of the endotoxins will of course depend on the *Bacillus thuringiensis* strain to be tested. Generally speaking, the test system can be used to evaluate the channel forming ability of an endotoxin from any strain of *Bacillus thuringiensis*. The Bt-type protein endotoxin may be a lepidopteran-active P-1 (CryI), lepidopteran/-dipteran-active P-2 (CryII), coleopteran-active CryC (CryIII), or dipteran-active cryD (CryIV) crystal protein. Bt endotoxin that exists in protoxin form, e.g., the P-1 (CryI) type proteins, must be converted into the activated toxin form, and this may be accomplished in the usual way by using proteases, e.g., trypsin.

The respective amounts of endotoxin and phospholipid that are employed to form the endotoxin-containing phospholipid bilayer can vary widely. The weight ratio of phospholipid to endotoxin is preferably within the range of about 5000:1 to 5:1. Ratios of phospholipid:endotoxin within the range of 100:1 to 5:1 contain relatively large amounts of endotoxin and are especially preferred for vesicles intended for use in the insecticidal compositions of this invention.

In situations where the phospholipid bilayer is in the form of a vesicle, the phospholipid is typically mixed with the endotoxin in an aqueous medium in a ratio of about 10–100 mg/ml phospholipid to about 1–50 µg/ml endotoxin, with a preferred composition weight ratio being about 5000:1 to 5:1 phospholipidendotoxin. The precise ratios may be varied depending on the phospholipid being used and the toxin being evaluated.

In another embodiment, the phospholipid-toxin mixture is supplemented with other proteins, particularly a brush border membrane protein which is derived from the epithelial cells of a particular insect of interest. This permits the preparation of a hybrid vesicle or planar bilayer which will more closely mimic the natural environment in which the delta-endotoxin will be expected to perform.

In such cases, the amounts of phospholipid and insect midgut brush border should be present in amounts that yield a hybrid phospholipid bilayer in which the phospholipid:brush border weight ratio is in the range of about 2000:1 to 250:1. The amount of brush border should be at least equal in amount to that of endotoxin incorporated into the hybrid phospholipid bilayer. The brush border is obtained from epithelial cells from the midgut of a suitable target insect, using conventional methods to isolate the brush border. The brush border membrane may be used as such or may be in the form of purified membrane components. When the hybrid phospholipid vesicle is intended for use in an insecticide formulation, rather than in the assay, the endotoxin may be mixed with phospholipid in an aqueous medium, with about 10-10,000 μg/ml of endotoxin being combined with about 10-100 mg/ml of phospholipid.

Regardless of the source of phospholipids, any convenient procedure can be used to form the vesicles. A particularly useful procedure is that of Racker (*Biochem.Biophys.Res.Com.*, 55:224, 1973) which involves quick-freezing the phospholipid/delta-endotoxin mixture in a dry ice/acetone bath, and subsequently thawing and sonicating the mixture. The resultant vesicles are of a size ideally suited for the assay. Numerous other methods for the manufacture of phospholipid vesicles have also been described, for example, the methods described by Brunner et al. (*Biochem.Biophys.Acta* 455:322-331, 1976), Tse et al. (*J.Biol.Chem.* 260:3506-3511, 1985), Racker (*Proc. 10th FEBS Meeting*, pp.25-31, 1975), and Jackson et al. (*Biochemistry* 21:5601-5608, 1982).

The preparation of phospholipid planar bilayers is also well known, and conventional techniques described in the literature may be utilized to form planar bilayers for use in this invention.

5.3. Measurement of Channel Quality

The phospholipid vesicles or planar bilayers formed by the procedures described in Section 5.2. will form an ion channel for monovalent cations such as $K^+$, $Na^+$, $Rb^{30}$, $Li^+$ and $H^+$, due to the presence of the delta-endotoxin in the phospholipid bilayer membrane. The quality of these ion channels can be assayed in vitro by measuring cation flow, using any number of parameters including, but not limited to, rate of cation uptake or efflux in vesicles, total quantity of cation flowing through the ion channels, cation specificity, and sensitivity of cation flow to inhibition by $Ba^{2+}$ or other ion channel blockers. Ion channel formation may also be evaluated indirectly, without direct measurements of monovalent cation flow, by measuring osmotic pressure-driven water flow through the ion channels.

Evaluation of the channel forming capacity of endotoxin is preferably performed in vesicles by the measurement of monovalent cation flow of an appropriate labelled cation. Although the most logical method of evaluation of channel formation is to directly measure $K^+$ uptake by the vesicles, the $^{42}K^+$ ion has a very short half-life, and is therefore not as well suited to the procedure as would be desired. Therefore, the use of an ion of similar biological behavior and size is preferred. This ion should be labeled in a way which permits easy measurement. One ion meeting these criteria is a radioactive isotope rubidium, $^{86}Rb^+$. Such an ion is similar electronically to $K^+$ and has a half-life in excess of 18 days, sufficiently long to permit manufacture and storage of $^{86}Rb^+$ salts in advance of use. The presence of this material can be detected, both quantitatively and qualitatively, by radiometric means such as scintillation counting. In addition material is taken up by insect cells at approximately the same rate and, presumably by the same mechanism as $K^+$ (English and Cantley, *J.Cell.Phys.*, 121:125-132, 1984). Other monovalent cations may be used to monitor the quality of the channel formed by the delta-endotoxins since the endotoxin-created ion channels are not totally specific for one monovalent cation. However, $K^+$ is the primary cation in the insect gut and is physiologically more important in the mode of action of the toxin. Therefore, $^{42}K^+$, and preferably $^{86}Rb^{30}$, are the labels of choice for this assay.

In an assay, thus, the presence of $^{86}Rb^+$ can be conveniently determined. In such a procedure, the phospholipid vesicles with endotoxin incorporated within the bilayer are mixed with an aqueous solution of $^{86}Rb^{30}$, or other labeled ions and measurements are taken beginning immediately after exposure. In one approach, the amount of cation absorbed by the vesicles, i.e., that passes into the interior via the ion channels, can be assayed by removing all non-absorbed cation, e.g., by passing the solution through a cation exchange column, and measuring the quantity of ion remaining trapped in the vesicles. Suitable cation exchange columns include, but are not limited to Dowex cation exchange resins, Amberlite Amberlyst resins, and Chelex resins. If a rate determination is desired, this can be accomplished by periodically removing aliquots from solution and calculating the amount absorbed as a function of time.

The monovalent cation flow may be measured directly, as described above, or indirectly. In the latter case, this may be accomplished by measurements of water flow into or out of the vesicles, which is induced by osmotic pressure differences across the vesicle bilayer. Such water flow usually correlates with monovalent cation flow and is conveniently measured via monitoring size change of the vesicles. This may be accomplished through continuous measurements obtained from spectrophotometric light scattering. Such light scattering measures the rate of vesicle size change, i.e., vesicle swelling or shrinking. This monitoring procedure has the advantage of not requiring periodic sampling of the vesicles.

Direct measurements of monovalent cation flow through the endotoxin-created ion channels in phospholipid vesicles can also be determined via ion concentration inside the vesicles, by fluorescence intensity, UV-visible spectrophotometry, flame photometry-atomic absorption, nuclear magnetic resonance spectroscopy, or X-ray microanalysis. In situations where a phospholipid planar bilayer is used, monovalent cation flow can be determined by electrophysiological techniques, e.g., voltage differences.

In the method of this invention, the evaluation of monovalent cation flow across the endotoxin-created ion channels should be carried out at a temperature of about 15° C. to 35° C. At temperatures well below 15° C. ion channel formation cannot be measured by the preferred cation flow measurement procedures described above. Above 35° C., many phospholipids are close to their melting points, precluding reliable formation of phospholipid vesicles.

The pH of the aqueous solution in contact with the endotoxin-containing phospholipid bilayer is preferably maintained through use of a buffered solution. The pH is preferably maintained within the range of 7.5 to 10. At acidic pH values, precipitation of the endotoxin protein may occur, and at highly alkaline pH values, degradation of the protein may occur.

In all of these procedures, the cation flow for the endotoxin-containing bilayer should be compared with that of a control, an endotoxin-free phospholipid bilayer or an otherwise identical phospholipid bilayer containing a second Bt-type protein endotoxin in lieu of the first endotoxin. By this manner, the propensity of the first endotoxin for forming an ion channel open to monvalent cation flow may be determined.

In the basic assay method of this invention, only one function of the delta-endotoxin, its channel forming capability, is assayed, so the toxins can be improved or specifically altered to adjust this function by manipulation of the regions of the protein responsible for producing the ion-channel capacity. The ability to assay for this specific activity did not exist previously because this function of delta-endotoxin had not previously been recognized. With the recognition of this property, it is now possible to selectively isolate and produce toxins having enhanced channel forming capabilities.

The preferred method of this invention, which involves the addition of brush border to the phospholipid bilayer to produce a hybrid phospholipid bilayer, yields further useful information about the mode of action of Bt endotoxins. The method measures the ability of the brush border receptor cells from the target insect to bind a particular Bt endotoxin protein, along with propensity of such endotoxin for forming an ion channel.

These aspects of the invention are illustrated in the following examples.

6.0 EXAMPLES

6.1. Assay of Delta Endotoxin Isolated from *Bacillus thuringiensis* Strain Hd263-8

Phospholipid vesicles were made by mixing soybean phospholipids (soy lecithin granules, Nature Food Centers, Wilmington, MA) 80 mg/ml in 6 mM of KCl, 100 mM imidazole-HCl, at pH 7.5. The phospholipid mixture was divided into two portions, one of which was supplemented with 3 μg delta-endotoxin (1μl) from *Bacillus thuringiensis* in 6 mM of KCl, 200 mM imidazole-HCl, at pH 7.5 and 1 μl 6mM KCl, 100 mM imidazole-HCl, at pH 7.5. The delta-endotoxin was prepared from a sporulated culture of *B. thuringiensis* strain HD263-8. Crystalline protoxin from this Bt source was isolated by renografin gradient according to the method of Milne et al. (*J.Invert.Path.* 29:230-231, 1977). This protoxin was activated by incubation with trypsin, 0.1 mg/ml, for 10 minutes at 37° C., and activated toxin was separated and collected from an ion exchange column according to the purification method of Bulla et al. (*J.Biol.Chem.* 256:3000-3004, 1981).

The two phospholipid mixtures were then quick frozen in dry ice/acetone, thawed, and sonicated for 30 seconds to form phospholipid vesicles, one group with endotoxin-containing vesicles and the other (control) vesicles not having been treated with endotoxin. Each group of vesicles (50 μl) was then added to 1.2ml of 20mM KCl, 5-10 μCi $^{86}Rb^+$ (as RbCl), imidazole-HCl, at pH 7.4. Two sets of experiments were carried out at separate temperatures, 0° C. and 22° C.

Figure 1:
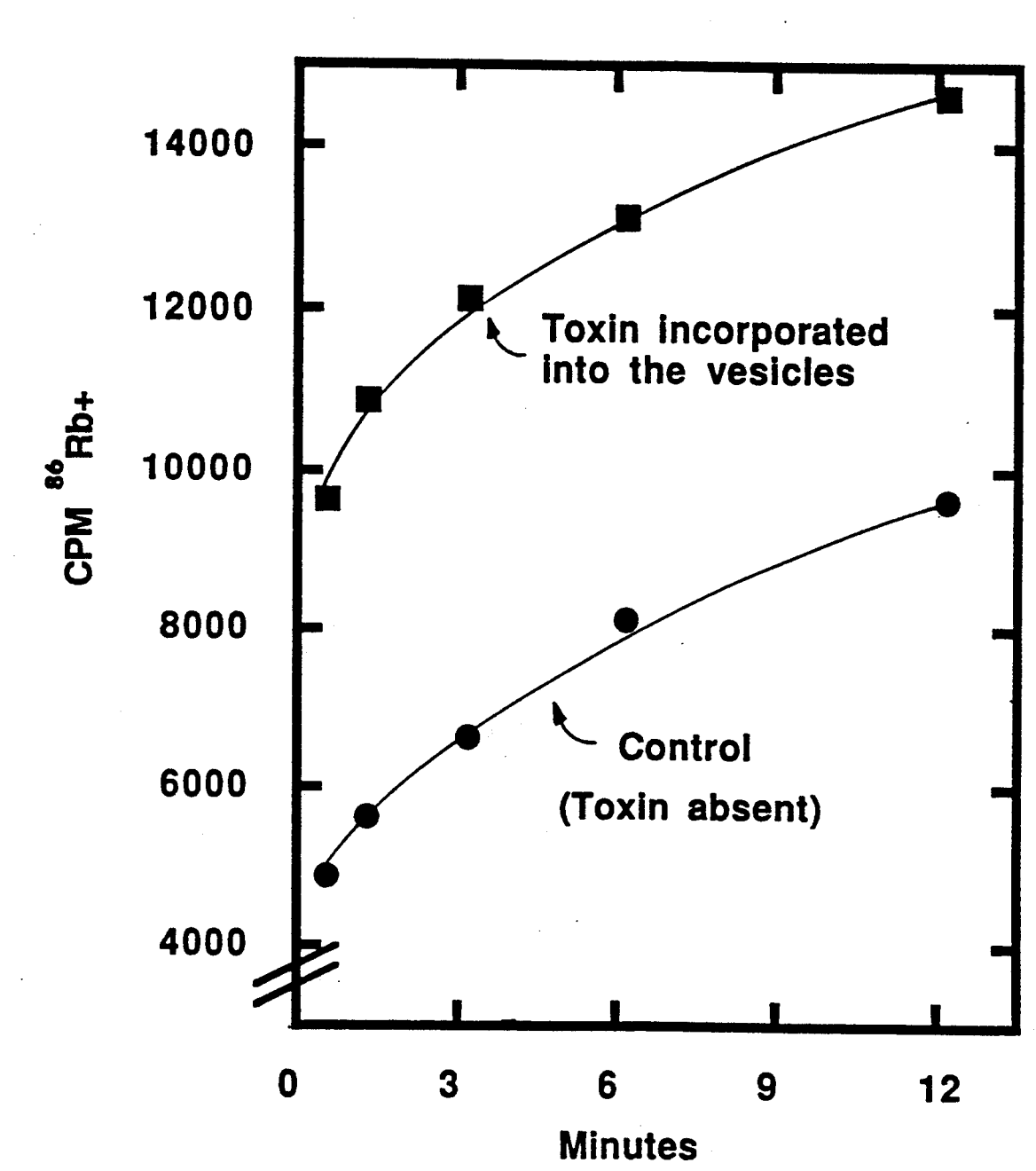

The endotoxin-containing vesicles and control vesicles in both sets of experiments were evaluated for monovalent cation uptake over a period of about twelve (at 22° C.) to twenty (at 0° C.) minutes, using radiolabelled $^{86}Rb^+$. At periodic intervals in each of these experiments, a 200 μl aliquot was removed from each vesicle mixture and passed through a 10 cm×6 mm ID Dowex-cation exchange column (This column absorbs from the aliquot mixture all $^{86}Rb^+$ not tightly bound or internalized in the vesicles). The vesicles were flushed through the column with 2 ml of 0.1 M sucrose and the radiolabeled cation content of the vesicles in the eluent counted by liquid scintillation. The eluent radioactivity measured for each of the aliquot samples, indicative of trapped $^{86}Rb^+$ contained within the vesicles in the aliquot, was utilized to determine the rate of $^{86}Rb^+$ influx and the total amount of trapped $^{86}Rb^+$ in the phospholipid vesicles. The results are presented in FIGS. 1 and 2, respectively. In both Figures, values for the counts per minute (CPM) of vesicle-trapped radiolabelled $^{86}Rb^+$ in the aliquot samples are plotted as a function of time at which the aliquot sample was taken. (Note: the data discussed here are expressed in counts per minute and not normalized to vesicle number or the specific activity of $^{86}Rb^+$ used in the assay; therefore, the total number of counts varies between figures and is indicative of different experiments and the different specific activity of $^{86}Rb^+$ at the time of the experiment). Two curves are shown in each of FIGS. 1 and 2: one for endotoxin-containing phospholipid vesicles and one for the control (endotoxin-free) vesicles.

As shown in FIG. 1 for the experiments performed at 22° C., the vesicles made with delta-endotoxin demonstrated both an enhanced rate of $^{86}Rb^+$ uptake, which is substantially completed within the first 0.5 minute, and an enhanced level of $^{86}Rb^+$ trapped, as compared with the control vesicles. These data indicated either of two conclusions: an enhanced ion permeability of vesicles made with the toxin or an ion channel formed in these vesicles because of the toxin. Confirmation that the latter is actually the case was obtained from the results generated at the lower temperature of 0° C. It should be evident from the results in FIGS. 1 and 2 that vesicles without toxin-created ion channels are cation permeable;for this reason, a control is employed in this invention.

As shown in FIG. 2 for the experiments performed at 0° C., vesicles with and without toxin exhibited similar permeability to the monovalent cation, $^{86}Rb+$. Vesicles made in the presence of toxin appeared slightly less permeable than those made without the toxin. These data suggest that the toxin does not simply make the vesicles more permeable (leaky) to the $^{86}Rb^+$ ion tracer, since generally, a leaky vesicle will be leaky at all temperatures. Instead, the toxins incorporated into the phospholipid vesicle appear to create a temperature-sensitive ion channel that is open at 22° C., and closed at 0° C.

6.2. Effect of BaCl₂ on Channel Formation

To determine the effect of $Ba^{2+}$ on channel formation, 50 μl phospholipid vesicles made as described in Section 6.1, both with and without endotoxin incorporated therein, were added to 1.2 ml 20 mM KCl, 5 mM BaCl₂, 5-10 μCi $^{86}Rb^{30}$, and 100 mM imidazole-HCl, at pH 7.5 and at 22° C. As in Section 6.1, the two groups of phospholipid vesicles were evaluated for monovalent cation uptake using $^{86}Rb^+$. At intervals in each set of experiments, aliquots (200 μl) were removed and added to a 10 cm×6 mm ID Dowex cation exchange column and eluted with 2 ml 0.1 M sucrose. The radiolabelled cation content of the vesicles in the eluent was counted by liquid scintillation.

Figure 3:
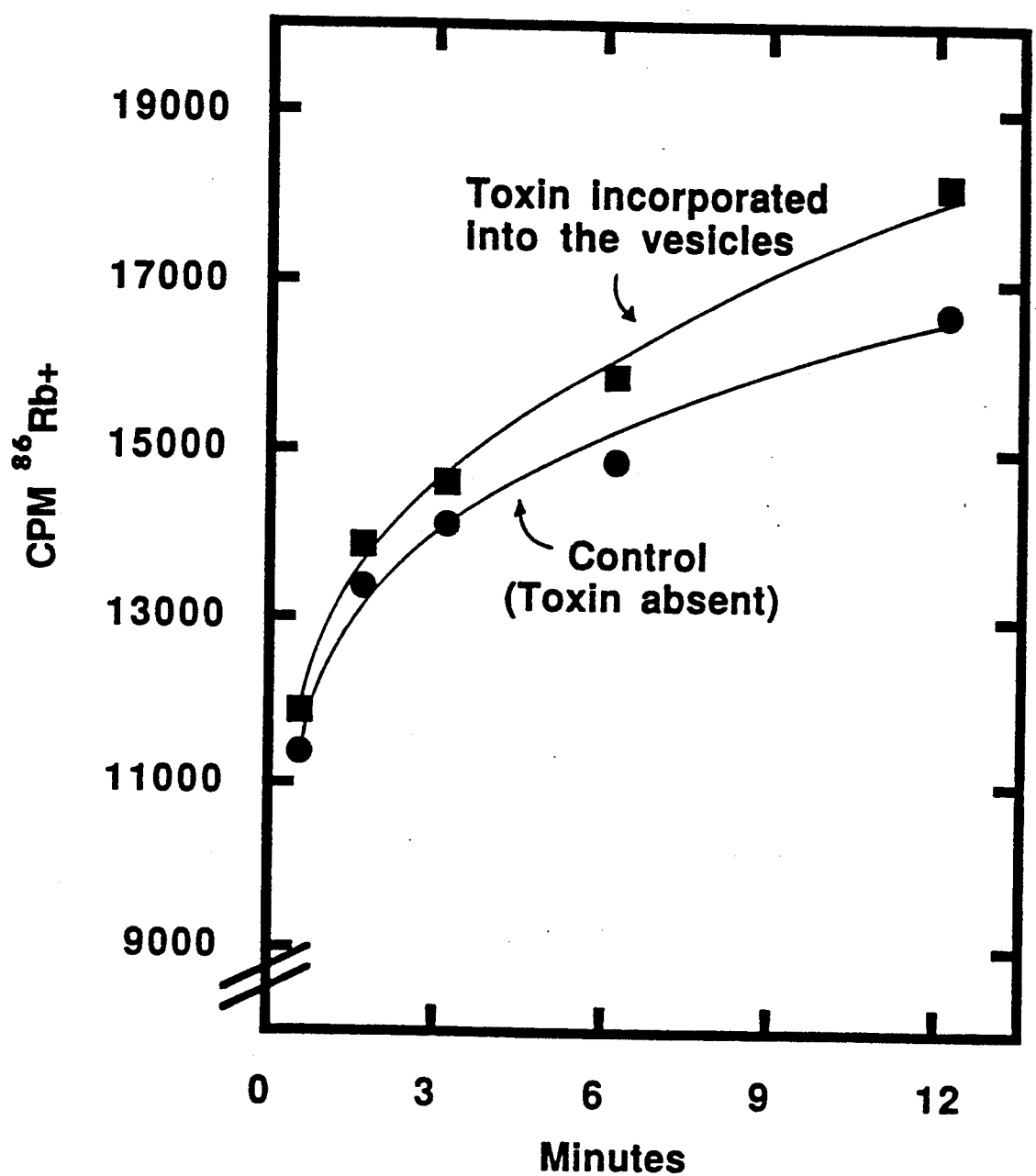
FIG. 3 illustrates the pattern of uptake of $^{86}Rb^+$ in the presence of $BaCl_2$ into phospholipid (soybean) vesicles containing Bt kurstaki activated endotoxin incorporated therein, compared with endotoxin-free vesicles.

The results are presented in FIG. 3, in the same manner used for FIGS. 1 and 2. As shown in FIG. 3, the results are similar for both sets of experiments. $Ba^{2+}$ effectively inhibited both the rate of $^{86}Rb^+$ uptake and the total level of $^{86}Rb^+$ in vesicles made with the toxin, as compared with the endotoxin-free control vesicles. These data suggest that the monovalent cation ion channel is formed in the phospholipid vesicles made with delta-endotoxin but that this ion channel is sensitive to, or blocked by, the divalent cation $Ba^{2+}$.

6.3. Channel Formation at Alkaline pH

The midgut lumen of lepidopteran insects is relatively alkaline ranging between pH 9 and 11. It was therefore important to ascertain whether the toxin would form an ion channel under these alkaline conditions.

Purified phosphatidyl choline (100 mg/ml) was mixed in a solution of 30 mM $K^+$ cholate, 10 mM 3-[cyclohexyl amino] 1-propanesulfonic acid (CAPS) buffer pH 9.5 with NaOH. Vesicles were made by cholate removal using the method described by Brunner et al., Biochem.Biophys.Acta 455:322-331 (1976). Trypsin-activated delta-endotoxin (50 μg) obtained and prepared in the manner described in Section 6.1, was dissolved in 50 μl CAPS-NaOH pH 9.5 and added to one ml of the phosphatidylcholine vesicles to a concentration of 50 μg/ml, mixed frozen in dry ice acetone, thawed and sonicated for 30 seconds, to produce endotoxin-containing phospholipid vesicles. Control phosphatidyl choline vesicles were treated with 50 μl CAPS-NaOH pH 9.5 before freeze-thaw sonication.

The endotoxin-containing phospholipid vesicles and control (endotoxin-free) phospholipid vesicles were then evaluated for cation uptake over a period of about eight minutes, using radiolabelled $^{86}Rb^+$. Uptake of $^{86}Rb^+$ was initiated by the addition of $^{86}Rb^+$ (10 μCi) in 100 μl 500 mM KCl, 10 mM CAPS pH 9.5, at a temperature of about 22° C. Aliquots (200 μl) were removed periodically and eluted through a Dowex cation exchange column with 2 ml 0.1 M sucrose, 0.1 M imidazole, pH 7.5, to remove any $^{86}Rb^+$ on the exterior of the vesicle. The trapped $^{86}Rb^+$ contained in the phospholipid vesicles was evaluated by liquid scintillation counting.

Figure 4:
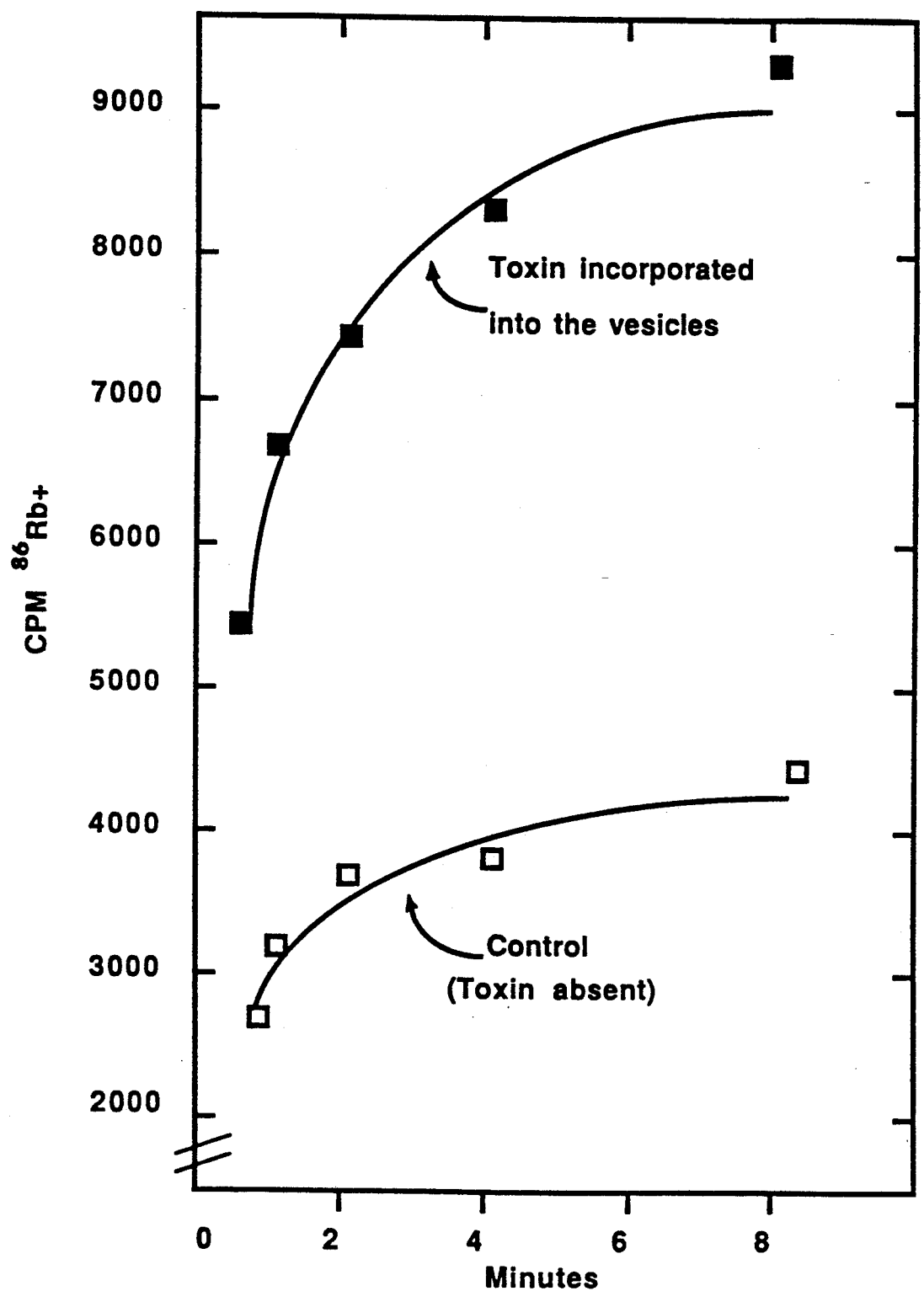
FIG. 4 illustrates the pattern of uptake of $^{86}Rb^+$ at about 22° C. and an alkaline pH of 9.5 into phospholipid (phosphatidyl choline) vesicles containing Bt kurstaki activated endotoxin incorporated therein, compared with endotoxin-free vesicles.

The results are presented in FIG. 4, in which values for the counts per minute (CPM) of vesicle-trapped $^{86}Rb^+$ in the aliquot samples are plotted as a function of sampling time. Two curves are shown: one for endotoxin-containing phospholipid vesicles and the other for the control (endotoxin-free) vesicles.

The results shown in FIG. 4 indicate that the rate of $^{86}Rb^+$ uptake and the total volume of trapped $^{86}Rb^+$ in the vesicles with the incorporated toxin were substantially greater than the values obtained for the control vesicles. The toxin appeared to be solely responsible for formation of an ion channel in the phosphatidyl choline vesicles at pH 9.5 used in this example; this is similar to the results obtained at pH 7.5 with soybean phospholipids, described in Section 6.1 and shown in FIG. 1.

6.4. External Addition of Endotoxin to Phospholipid Vesicles

Purified phosphatidyl choline vesicles were prepared as described in Section 6.3, and subjected to freeze-thaw sonication in the absence of delta-endotoxin to produce endotoxin-free phospholipid vesicles. Trypsin-activated delta-endotoxin (50 μg), obtained and prepared as in Section 6.1., was subsequently added to a one ml pool of vesicles and allowed to incubate 40 min. at 22° C. to expose the endotoxin to the exterior of the endotoxin-free phospholipid vesicles.

The endotoxin-exposed phospholipid vesicles and control phospholipid vesciles (no endotoxin exposure) were then evaluated for cation uptake over a period of about eight minutes using radiolabelled $^{86}Rb^+$. The cation flow assay was initiated by the addition of $^{86}Rb^+$ (10 μCi) in 100 μl of 500 mM KCl, 10 mM CAPS pH 9.5, at a temperature of about 22° C. Periodically aliquots of the sample were poured through a Dowex cation exchange column and eluted with 0.1 M sucrose 0.1 M imidazole at pH 7.5, to remove any 86Rb+ on the exterior of the vesicles. The trapped $^{86}Rb^+$ contained in the vesicles was counted by liquid scintillation.

Figure 5:
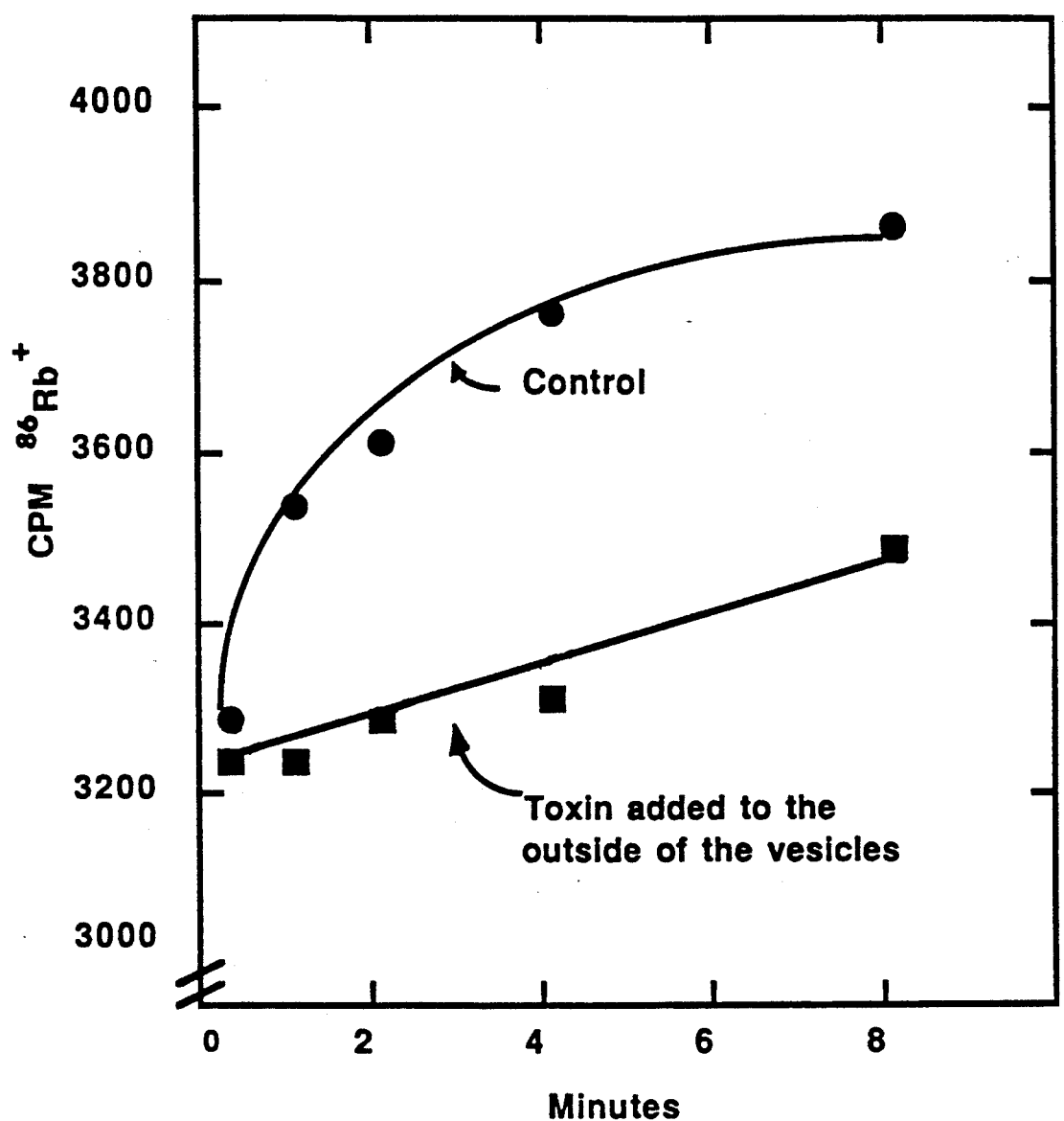
FIG. 5 illustrates the pattern of uptake of $^{86}Rb^+$ into phospholipid (phosphatidyl choline) vesicles having Bt kurstaki activated endotoxin added to the outside of the vesicles, compared with endotoxin-free vesicles.

The results are illustrated in FIG. 5, in which values the counts per minute (CPM) of vesicle-trapped $^{86}Rb^+$ in the aliquot samples are plotted as a function of sampling time. Two curves are shown: one for the endotoxin-exposed phospholipid vesicles and the other for the control vesicles.

The results shown in FIG. 5 indicate that the toxin, when added to the outside of the vesicles, failed to enhance the rate of $^{86}Rb^+$ uptake. In fact, the toxin actually impeded the rate of $^{86}Rb^+$ diffusion into the endotoxin-exposed vesicles, as compared with the results obtained with the control vesicles. These results demonstrate that incorporation of the endotoxin into the vesicle is critical for the assay method.

6.5 Protocol for Comparative Toxicity Assay of Two BT-Type Protein Endotoxins in Susceptible Insects For evaluation of the ion channel formation properties of delta endotoxins from *Bacillus thuringiensis* in the method of this invention, it is necessary for the toxins to be incorporated into a phospholipid membrane environment. A simple lipid bilayer made from phosphatidyl choline is sufficient to evaluate the ion channel property of the toxin. A phosphatidyl choline bilayer in the form of a phospholipid vesicle (liposome) is formed spontaneously when a film of dried phosphatidyl choline is mixed with an aqueous buffered solution. Toxin in activated form, in aqueous solution, is then added to the phospholipid vesicle suspension and incorporated into the membrane bilayer by a freeze-thaw-sonication procedure.

Subsequent exposure of the toxin-containing phospholipid vesicles to a monovalent cation concentration gradient will force movement of the cation species into the vesicles, provided that the vesicles are cation-permeable. This monovalent cation movement will continue until an equilibrium is established, and the method of this invention relies on measurements of the cation flow taken prior to such equilibrium being achieved, to determine the propensity of a given protein endotoxin for forming an ion channel.

The use of an isotope tracer like the monovalent cation $^{86}Rb^+$ allows the concentration of radiolabelled cation inside the vesicles to be measured, as the monovalent cation flows into the vesicles. Periodic sampling of vesicles allows the cation flow to be measured. Cations on the exterior of the sampled vesicles are removed by exposing the vesicles to a Chelex cation exchange column. Cations trapped inside the sampled vesicles are measured indirectly, via use of a liquid scintillation counter to count the isotopic decay signal.

The cation flow rate is determined by plotting the scintillation count data as a function of vesicle sample time. Relative protein endotoxin toxicities, are determined by comparing the monovalent cation flow for different Bt protein endotoxins under otherwise similar conditions. In susceptible insects, the more potent endotoxin protein will evidence a higher monovalent cation flow rate, i.e., ion channels being present in greater numbers or allowing more efficient cation flow.

The following protocol may be used in the method of this invention:

1. The phospholipid, 100 mg phosphatidyl choline, is mixed with 1 ml buffered aqueous solution (50 mM CAPS pH 9.5) at a temperature of 20°-25° C., using a Vortex mixer, until the aqueous phospholipid vesicle suspension is visibly homogeneous.

2. The activated Bt protein endotoxin of interest is solubilized in an aqueous potassium hydroxide solution (12 mM KOH) at a temperature of 20°-25° C., in amounts sufficient to provide a final concentration of 100 µg protein endotoxin/µl.

3. A portion of the solubilized toxin from step 2, in an amount of 1 µl (containing 100 mg dissolved toxin), is added to 100 µl of the phospholipid vesicle suspension from step 1 and mixed using a Vortex mixer.

4. The mixture from step 3 is frozen for a short time in a dry ice/acetone bath, thawed and warmed to a temperature of about 25° C., and then sonicated for 30 seconds, to form phospholipid vesicles with toxin incorporated therein, in an aqueous suspension.

5. The toxin-treated vesicle mixture from step 4 is added to an aqueous solution of $^{86}Rb^+$ (10 µCi in 50 mM KCl), in an amount of 1000 µl. This addition of the vesicle mixture is considered to occur at time=0.

6. At one-half minute intervals beginning from t=0 and occurring over a ten minute period, 200 µl portions are removed from the vesicle suspension formed in step 5.

7. Each vesicle sample portion is introduced into individual Chelex cation exchange columns, to bind cations in the sample portion and on the exterior of the vesicles. The vesicles are thereafter eluted from the columns with 2 ml 0.1 M aqueous sucrose solution.

8. The eluent from each column is collected and the amounts of trapped $^{86}Rb^+$ in the eluted vesicles is measured using a liquid scintillation counter.

9. The scintillation count data are then plotted as a function of vesicle sampling time over the ten minute sampling period.

10. The procedure of steps 1-9 is repeated for a second Bt protein endotoxin, to generate comparative data for evaluating the relative toxin potencies in susceptible insects.

11. As an alternative to step 10 or in addition to step 10, a control, i.e., a toxin-free baseline, may be generated by repeating steps 1-9 but with steps 2 and 3 (involving toxin solubilization and incorporation into the phospholipd vesicles) being omitted. In step 4, 100 µl of the phospholipid vesicle suspension from step 1 is used.

12. In order to evaluate the relative toxicities of the Bt-type protein endotoxins, comparisons between the plotted results should be made using data obtained for the sampling intervals between 4-8 minutes.

6.6 Protocol for Comparative Toxicity Assay of Two BT-Type Protein Endotoxins in a Specific Target Insect Brush border membrane from a specific target insect, e.g., *Heliothis zea* larvae, may be utilized in the method of this invention to evaluate the susceptibility of the target insect to Bt endotoxin proteins. Brush border membrane from a target insect contains receptor cells that serve to recognize certain Bt endotoxin proteins and facilitate binding of the protein to the receptor.

Phospholipid vesicles formed with brush border membrane as part of their structure are capable of catalyzing incorporation of a Bt endotoxin protein into the phospholipid membrane bilayer. In this manner, ion channels are formed in the vesicle, and measurements of monovalent cation flow may be made as described in the previous section. Brush border membrane can be incorporated into phospholipid vesicles by subjecting an aqueous suspension of phospholipid vesicles and brush border membrane to a freeze-thaw-sonication procedure.

These hybrid phospholipid vesicles (i.e., phosphatidyl choline vesicles having brush border membrane incorporated therein) in an aqueous suspension, are then contacted with the endotoxin protein of interest. The monovalent cation flow into such hybrid vesicles is thereafter measured by use of an isotope tracer like $^{86}Rb^{30}$, in the manner described in the previous section.

The susceptibility of a particular target insect, whose brush border membrane is being studied, is evaluated with different Bt endotoxin proteins to determine their relative insecticidal potencies. The following protocol may be used:

1. Mix 100 mg phosphatidyl choline with 1 ml buffered aqueous solution (50 mM CAPS pH 9.5) at a temperature of 20°-25° C. using a Vortex mixer, until the aqueous phospholipid suspension is visibly homogeneous.

2. Brush border membrane from a suitable target insect is obtained using the general procedure described by barbarat et al., *J.Biol.Chem* (1986) 261:14455-14460.

3. A portion of the brush border membrane in aqueous suspension containing 10 µg brush border membrane/10 µl in an amount containing 300 µg of brush border membrane, is added to 100 µl of the phospholipid suspension from step 1 and mixed using a Vortex mixer.

4. The mixture from step 3 is frozen for a short time in a dry ice/acetone bath, thawed and warmed to a temperature of about 25° C., and then sonicated for 30 seconds to form hybrid phospholipid vesicles, in an aqueous suspension.

5. Activated Bt protein endotoxin of interest is solubilized in an aqueous potassium hydroxide solution (12 mM KOH) at a temperature of 20°-25° C., in amounts sufficient to provide a final concentration of 100 µg protein endotoxin/µl.

6. A portion of the solubilized toxin from step 5, in an amount of 1 µl (containing 100 µg dissolved toxin) is added to the aqueous suspension of hybrid phospholipid vesicles from step 4.

7. The toxin-treated vesicles from step 6 is added to an aqueous solution of $^{86}Rb^+$ (10 µCi in 50 mM KCl), in an amount of 1000 µl. This addition of the vesicles is considered to occur at time=0.

8. At one-half minute intervals beginning from t=0 and occurring over a ten minute period, 200 µl portions are removed from the vesicle suspension formed in step 7.

9. Each vesicle sample portion is introduced into individual Chelex cation exchange columns, to bind cations in the sample portion and on the exterior of the vesicles. The vesicles are thereafter eluted from the columns with 2 ml 0.1 M aqueous sucrose solution.

10. The eluent from each column is collected and the amount of trapped $^{86}Rb^+$ in the eluted vesicles is measured using a liquid scintillation counter.

11. The scintillation count data are then plotted as a function of vesicle sampling time over the ten minute sampling period.

12. The procedure of steps 1-11 is repeated for a second Bt protein endotoxin, to generate comparative data for evaluating the relative toxin potencies in the insect whose brush border membrane is being studied.

13. As an alternative or in addition to step 12, a control, i.e., a toxin-free baseline, may be generated by repeating steps 1-11 but with steps 5 and 6 (involving toxin solubilization and toxin-treatment of the phospholipid vesicles) being omitted. In step 7, 100 μl of the hybrid phospholipid vesicle suspension from step 4 is used.

14. In order to evaluate the relative toxicities of the Bt-type protein endotoxins in the target insect being studied, comparisons between the plotted results should be made using data obtained for the sampling intervals between 4-8 minutes.

It is apparent that many modifications and variations of this invention as hereinabove set forth may be made without departing from the spirit and scope thereof. The specific embodiments described are given by way of example only, and the invention is limited only by the terms of the claims.

What is claimed is:

1. An in vitro method for evaluating the relative toxicities of *Bacillus thuringiensis*-type protein endotoxins in susceptible insects, which comprises
   (i) combining a phospholipid and a Bt-type protein endotoxin, in activated form, under conditions in an aqueous medium that produce a phospholipid bilayer containing endotoxin incorporated therein;
   (ii) contacting one side of the endotoxin-containing phospholipid bilayer with an aqueous solution containing a monovalent cation to create an ion concentration gradient across the bilayer, at a temperature of from about 15° C. to 35° C.;
   (iii) measuring the monovalent cation flow across the endotoxin-containing phospholipid bilayer; and
   (iv) comparing the cation flow for the endotoxin-containing bilayer with that of a control, selected from an endotoxin-free phopholipid bilayer or an otherwise identical phospholipid bilayer containing a second Bt-type protein endotoxin in lieu of the first endotoxin;
   whereby the propensity of the first protein endotoxin for forming an ion channel open to monovalent cation flow is determined.

2. An in vitro method for evaluating the relative toxicities of *Bacillus thuringiensis*-type protein endotoxins in target insects, which comprises
   (i) combining insect midgut brush border from a specific target insect and a phospholipid, under conditions in an aqueous medium that produce a hybrid phospholipid bilayer which incorporates the brush border therein;
   (ii) introducing a Bt-type protein endotoxin, in activated form, into contact with the hybrid phospholipid bilayer, so as to bind the endotoxin into the hybrid phospholipid bilayer;
   (iii) contacting one side of the endotoxin-treated hybrid phospholipid bilayer with an aqueous solution containing a monovalent cation to create an ion concentration gradient across the bilayer, at a temperature from about 15° C. to 35° C.;
   (iv) measuring the monovalent cation flow across the endotoxin-treated hybrid phospholipid bilayer; and
   (v) comparing the cation flow for the endotoxin-treated hybrid phospholipid bilayer with that of a control, selected from an endotoxin-free hybrid phospholipid bilayer or an otherwise identical hybrid phospholipid bilayer treated with a second Bt-type protein endotoxin in lieu of the first endotoxin;
   whereby the susceptibility of the target insect to the first protein endotoxin and the propensity of such endotoxin for forming an ion channel open to monovalent cation flow are determined.

3. The method of claim 1 or 2 wherein the phospholipid bilayer is in the form of a phospholipid vesicle.

4. The method of claim 1 or 2 wherein the phospholipid bilayer is in the form of a planar lipid bilayer.

5. The method of claim 1 or 2 wherein the phospholipid and protein endotoxin are present in the phospholipid bilayer in a weight ratio of phospholipid to endotoxin within the range of about 5000:1 to 5:1.

6. The method of claim 2 wherein the phospholipid and insect midgut brush border are present in the hybrid phospholipid bilayer in a weight ratio of phospholipid to brush border within the range of about 2000:1 to 250:1, provided that the amount of brush border is at least equal to that of endotoxin.

7. The method of claim 1 or 2 wherein the aqueous medium is a buffered solution.

8. The method of claim 1 or 2 wherein the aqueous solution containing the monovalent cation is a buffered solution.

9. The method of claim 1 or 2 wherein the pH of aqueous solution in contact with the phospholipid bilayer is maintained above a pH which induces precipitation of the protein endotoxin and below a pH which induces degradation of the protein endotoxin.

10. The method of claim 9 wherein the pH of aqueous solution in contact with the phospholipid bilayer is maintained at a pH value within the range of about 7.5 to 10.

11. The method of claim 1 or 2 wherein the phospholipid is selected from the group of phosphatidyl choline, phosphatidyl ethanolamine, phosphatidyl inositol, phosphatidyl glycerol, phosphatidyl serine, soybean-derived phospholipids, insect-derived phospholipids, and mixtures thereof.

12. The method of claim 1 or 2 wherein the Bt-type protein endotoxin is selected from the group consisting of CryI (PI) protein endotoxins, CryII (P2) protein endotoxins, CryIII (CryC) protein endotoxins and CryIV (CryD) protein endotoxins.

13. The method of claim 1 or 2 wherein the monovalent cation is selected from the group consisting of $K^+$, $Na^+$, $Rb^{30}$, $Li^+$ and $H^+$.

14. The method claim 1 or 2 wherein the monovalent cation is radiolabelled.

15. The method of claim 3 wherein the monovalent cation flow is determined by spectrophotometric light scattering, scintillation counting of radiolabelled cations, fluorescence intensity, UV-visible spectrophotometry, atomic absorption, nuclear magnetic resonance or x-ray analysis.

16. The method of claim 4 wherein the monovalent cation flow is determined by electrophysiological techniques.

* * * * *